United States Patent
Montgomery

(10) Patent No.: US 7,189,385 B2
(45) Date of Patent: Mar. 13, 2007

(54) TOOTH WHITENING COMPOSITIONS

(75) Inventor: R. Eric Montgomery, Monterey, MA (US)

(73) Assignee: Discus Dental Impressions, Inc., Culver City, CA (US)

( * ) Notice: Subject to any disclaimer, the term of this patent is extended or adjusted under 35 U.S.C. 154(b) by 0 days.

(21) Appl. No.: 10/715,917

(22) Filed: Nov. 18, 2003

(65) Prior Publication Data

US 2004/0101497 A1    May 27, 2004

Related U.S. Application Data

(63) Continuation of application No. 09/840,844, filed on Apr. 24, 2001, now abandoned, which is a continuation of application No. 09/196,403, filed on Nov. 19, 1998, now Pat. No. 6,221,341.

(60) Provisional application No. 60/066,187, filed on Nov. 19, 1997.

(51) Int. Cl.
*A61K 8/22* (2006.01)
*A61K 8/38* (2006.01)

(52) U.S. Cl. ...................... 424/53; 433/215; 433/217.1; 424/48

(58) Field of Classification Search .................. 424/53, 424/401, 616; 433/215, 216
See application file for complete search history.

(56) References Cited

U.S. PATENT DOCUMENTS

| | | | | |
|---|---|---|---|---|
| 3,901,819 A | * | 8/1975 | Nakagawa et al. | 252/186.4 |
| 4,526,698 A | * | 7/1985 | Kuroda et al. | 510/305 |
| 5,279,816 A | * | 1/1994 | Church et al. | 424/53 |
| 5,885,554 A | * | 3/1999 | Michael et al. | 424/49 |
| 5,928,628 A | * | 7/1999 | Pellico | 424/49 |

* cited by examiner

*Primary Examiner*—Frederick Krass

(57) ABSTRACT

Novel compositions and methods are disclosed for cosmetically treating teeth in a manner to increase brightness or shade of the teeth. The compositions include a low molecular weight compound having a high acetyl group functionality useful in the production of a peroxy acid which then acts as a whitening agent.

32 Claims, No Drawings

TOOTH WHITENING COMPOSITIONS

CROSS-REFERENCES TO RELATED APPLICATIONS

This application is a continuation application of nonprovisional U.S. patent application Ser. No. 09/840,844 filed Apr. 24, 2001, now abandoned, which is a continuation of application Ser. No. 09/196,403, filed Nov. 19, 1998, now U.S. Pat. No. 6,221,341, which claims priority to U.S. Provisional Application No. 60/066,187, filed Nov. 19, 1997. All of the foregoing applications are hereby incorporated by reference to the extent permitted by law.

BACKGROUND OF THE INVENTION

1. Field of the Invention

Embodiments of the present invention relate in general to oral compositions, and more particularly, to tooth whitening compositions.

2. Description of Related Art

White teeth have long been considered cosmetically desirable. Unfortunately, due to the presence of chromogenic (color-causing) substances in food, beverages, tobacco, and salivary fluid, in addition to internal sources such as blood, amalgam restoratives, and antibiotics such as tetracycline, teeth become almost invariably discolored in the absence of intervention. The tooth structures that are generally responsible for presenting a stained appearance are enamel, dentin, and the acquired pellicle. Tooth enamel is predominantly formed from inorganic material, mostly in the form of hydroxyapatite crystals, and further contains approximately 5% organic material primarily in the form of collagen. In contrast, dentin is composed of about 20% protein including collagen, the balance consisting of inorganic material, predominantly hydroxyapatite crystals, similar to that found in enamel. The acquired pellicle is a proteinaceous layer on the surface of tooth enamel which reforms rapidly after an intensive tooth cleaning.

Staining of teeth results from extrinsic and/or intrinsic staining. Extrinsic staining of the acquired pellicle arises as a result of compounds such as tannins and other polyphenolic compounds which become trapped in and tightly bound to the proteinaceous layer on the surface of teeth. This type of staining can usually be removed by mechanical methods of tooth cleaning. In contrast, intrinsic staining occurs when staining compounds penetrate the enamel and even the dentin, or alternatively arise from sources within the tooth. This type of staining is not amenable to mechanical methods of tooth cleaning and chemical methods, which can penetrate into the tooth structure, are required. Intrinsic tooth staining is generally more intractable and difficult to remove than extrinsic tooth staining.

Consequently, tooth-bleaching compositions generally fall into two categories: (1) gels, pastes, or liquids, including toothpastes that are mechanically agitated at the stained tooth surface in order to affect tooth stain removal through abrasive erosion of stained acquired pellicle; and (2) gels, pastes, or liquids that accomplish the tooth-bleaching effect by a chemical process while in contact with the stained tooth surface for a specified period, after which the formulation is removed. In some cases, an auxiliary chemical process, which may be oxidative or enzymatic, supplements the mechanical process.

Among the chemical strategies available for removing or destroying tooth stains, the most effective compositions contain an oxidizing agent, such as hydrogen peroxide, in order to attack the chromogen molecules in such a way as to render them colorless, water-soluble, or both. In one of the most popular approaches to whitening a patient's teeth, a dental professional will construct a custom made dental bleaching tray for the patient from an impression made of the patient's dentition and prescribe the use of an oxidizing gel to be dispensed into the bleaching tray and worn intermittently for a period of from about 2 weeks to about 6 months, depending upon the severity of tooth staining. These oxidizing compositions, usually packaged in small plastic syringes or tubes, are dispensed directly by the patient into the custom-made tooth-bleaching tray, held in place in the mouth for contact times of greater than about 60 minutes, and sometimes as long as 8 to 12 hours. The slow rate of bleaching is in large part the consequence of the very nature of formulations that are developed to maintain stability of the oxidizing composition. The most commonly used oxidative compositions contain the hydrogen peroxide precursor carbamide peroxide which is mixed with an anhydrous or low-water content, hygroscopic viscous carrier containing glycerin and/or propylene glycol and/or polyethylene glycol. When contacted by water, carbamide peroxide dissociates into urea and hydrogen peroxide. Associated with the slow rate of bleaching in the hygroscopic carrier, the currently available tooth-bleaching compositions cause tooth sensitization in over 50% of patients. Tooth sensitivity is believed to result from the movement of fluid through the dentinal tubules, which is sensed by nerve endings in the tooth. The carriers for the carbamide peroxide enhance this movement. In fact, it has been determined that glycerin, propylene glycol and polyethylene glycol can each give rise to varying amounts of tooth sensitivity following exposure of the teeth to heat, cold, overly sweet substances, and other causative agents.

Prolonged exposure of teeth to bleaching compositions, as practiced at present, has a number of adverse effects in addition to that of tooth sensitivity. These include: solubilization of calcium from the enamel layer at a pH less than 5.5 with associated demineralization; penetration of the intact enamel and dentin by the bleaching agents, so as to reach the pulp chamber of a vital tooth thereby risking damage to pulpal tissue; and dilution of the bleaching compositions with saliva resulting in leaching from the dental tray and subsequent ingestion.

Alternatively, there are oxidizing compositions (generally those with relatively high concentrations of oxidizers) which are applied directly to the tooth surface of a patient in a dental office setting under the supervision of a dentist or dental hygienist. Theoretically, such tooth whitening strategies have the advantage of yielding faster results and better overall patient satisfaction; however, due to the high concentration of oxidizing agents contained in these so called "in-office" compositions, they can be hazardous to the patient and practitioner alike if not handled with care. The patient's soft tissues (the gingiva, lips, and other mucosal surfaces) must first be isolated from potential exposure to the active oxidizing agent by the use of a perforated rubber sheet (known as a rubber dam), through which only the teeth protrude. Alternatively, the soft tissue may be isolated from the oxidizers to be used in the whitening process by covering said soft tissue with a polymerizable composition that is shaped to conform to the gingival contours and subsequently cured by exposure to a high intensity light source. Once the soft tissue has been isolated and protected, the practitioner may apply the oxidizing agent directly onto the stained tooth surfaces for a specified period of time or until a sufficient change in tooth color has occurred. Typical results obtained through the use of a in-office tooth whitener, with or without activation by heat, range from about 2 to 3 shades (as measured with the VITA Shade Guide, VITA Zahnfarbik).

The range of tooth shades in the VITA Shade Guide varies from very light (B1) to very dark (C4). A total of 16 tooth shades constitute the entire range of colors between these two endpoints on a scale of brightness. Patient satisfaction with a tooth whitening procedure increases with the number of tooth shade changes achieved, with a generally accepted minimum change desirable of about 4 to 5 VITA shades.

Of the many peroxides available to the formulator of tooth whitening compositions, hydrogen peroxide (and its adducts or association complexes, such as carbamide peroxide and sodium percarbonate) has been used almost exclusively. The chemistry of hydrogen peroxide is well known, although the specific nature of its interactions with tooth chromogens is poorly understood. It is believed that hydrogen peroxide destroys tooth chromogens in a similar fashion to that observed in the destruction of laundry stains, that is, by oxidizing unsaturated carbon-carbon, carbon-oxygen, and carbon-nitrogen bonds found in the stain molecules. A related class of compounds, the peroxyacids, has been used in laundry detergents to effectively whiten clothes, due primarily to their stability in solution and their specific binding abilities to certain types of stain molecules. A number of stable, solid peroxyacids have been used, including diperoxydodecanoic acid and the magnesium salt of monoperoxyphthalic acid. Other peroxyacids, such as peroxyacetic acid, are available as solutions containing an equilibrium distribution of acetic acid, hydrogen peroxide, peroxyacetic acid and water. Alternatively, a peroxide donor such as sodium perborate or sodium percarbonate is formulated into a dry laundry detergent, together with a peroxyacid precursor. Upon contact with the wash water, the peroxide donor releases hydrogen peroxide into the wash solution, which then reacts with the peroxyacid precursor to form the actual peroxyacid. Examples of peroxyacids created in situ include peroxyacetic acid (from hydrogen peroxide and tetraacetylethylenediamine) and peroxynonanoic acid (from hydrogen peroxide and nonanoyloxybenzene sulfonate).

It is recognized in the art that the water solubility of the peroxyacid precursor is critical to the performance of a particular detergent composition. For example, rapidly soluble peroxyacid precursors tend to release the peroxyacid too quickly into solution, and as a result, may damage or not effectively clean the clothes being washed. Peroxyacid precursors that are slowly soluble in water, on the other hand, tend to give a prolonged and controlled release of peroxyacid into the wash water during the laundering cycle, and as a result, may more effectively clean clothing.

Peroxyacids have been used in oral care compositions to whiten stained teeth. U.S. Pat. No. 5,279,816 discloses a method of whitening teeth comprising the application of a peroxyacetic acid-containing composition having an acid pH. EP 545,594 A1 discloses the use of peroxyacetic acid in preparing a composition for whitening teeth. The peroxyacetic acid may be present in the composition, or in the alternative, may be generated in situ by combining a peroxide source with a peroxyacetic acid precursor during use. U.S. Pat. No. 5,302,375 discloses a composition that generates peroxyacetic acid within a vehicle in situ by combining water, acetylsalicylic acid and a water soluble alkali metal percarbonate.

BRIEF SUMMARY OF THE INVENTION

Embodiments of the present invention are directed to compositions and methods useful in cosmetically treating teeth in a manner to improve the brightness or shade of the teeth. Embodiments of the present invention are also directed to compositions having antimicrobial activity for use in the therapeutic treatment of teeth. According to one embodiment of the present invention, a method is described whereby a composition is provided which upon contact with an aqueous medium or environment generates peroxyacetic acid for use as an oxidant in the tooth-whitening or stain removal process. Embodiments of the present method invention advantageously utilize compounds capable of generating peroxyacids quickly and effectively for application to teeth as compared to prior art compounds.

The methods of the present invention employ compositions including at least one orally acceptable acyl group source or precursor and at least one orally acceptable peroxide source or precursor. The acyl group source and the peroxide precursor, upon contact with an aqueous solution, generate a peroxyacid. The acyl group source and the peroxide precursor may be dispersed within an anhydrous carrier.

According to one embodiment of the present invention, the acyl group source is an acetyl group source being a low molecular weight molecule having at least one acetyl group to be used in the formation of a peroxy acid. According to this embodiment, the acetyl group source has a molecular weight and steric configuration that allows the acetyl group source to penetrate pores present in teeth after application of the acetyl group source. Once the acetyl group source has penetrated a tooth, a peroxide source can then be used to generate a peroxyacid within a tooth rather than only on the surface of the tooth. More efficient and greater whitening capabilities are achieved by using such acetyl group sources capable of penetrating pores in teeth.

According to a specific embodiment of the present invention, the acetyl group source is a low molecular weight $C_1$–$C_5$ molecule having between 1 and 5 labile acetyl groups. In a acetyl groups. It is to be understood that labile functional groups having similar properties to acetyl groups are considered to be within the scope of the present invention, i.e. all that is required is that the active group be capable of forming an agent useful in the whitening or stain removal of teeth, such as a peroxyacid. Such labile functional groups include $C_1$–$C_5$ acyl containing groups.

According to one embodiment of the present invention, the composition includes at least two components: one component including a source of peroxide (such as hydrogen peroxide), and a second component including a source of acetyl groups. The two components may be mixed together prior to application of the resulting mixture to the tooth surface. Alternatively, each component may be sequentially applied directly to the tooth surface. It should be noted that either of the components may be applied first before the application of the remaining component.

One object of the present invention, therefore, is to provide a novel composition which quickly and effectively produces a peroxyacid in an amount sufficient to whiten teeth. Another object of the present invention is to provide a method whereby a peroxyacid generating species is allowed to penetrate into the tooth and beyond the tooth surface where staining compounds may be present and then generating a peroxyacid or other tooth-whitening species within the tooth to provide a greater tooth whitening effect.

Other objects, features and advantages of certain embodiments of the present invention will become more fully apparent from the following description taken in conjunction with the accompanying claims.

DETAILED DESCRIPTION OF CERTAIN PREFERRED EMBODIMENTS

The principles of the present invention may be applied with particular advantage to obtain compositions and methods for the whitening or stain removal of teeth. The present invention, in one embodiment, is directed to a composition that whitens the color of teeth when applied to a stained tooth surface. The composition may be provided as a multi-component formulation including a peroxide source and a source of acetyl or functionally similar groups, which when combined produces an active ingredient useful in teeth whitening, such as a peroxyacid. According to one embodiment, the peroxide source is hydrogen peroxide or a hydrogen peroxide percurser and the source of acetyl or functionally similar groups is a $C_1$–$C_5$ molecule having between 1 to 5 labile $C_1$–$C_5$ acyl containing groups.

Alternatively, in order to prevent premature reaction of the hydrogen peroxide or its precursor with the source of acetyl groups, an anhydrous formulation containing both the source of acetyl groups and hydrogen peroxide or its precursor is provided. The hydrogen peroxide or its precursor, and the the source of acetyl groups, upon placement against the stained tooth surface in the oral cavity, are activated by the aqueous content of the saliva to generate a peroxacid, such as peroxyacetic acid.

Alternatively, a composition may be manufactured having each of the hydrogen peroxide or its precursor and the source of acetyl groups as a separate and distinct component. According to this aspect of the invention, one component containing the source of acetyl groups may be applied to a stained tooth surface followed immediately thereafter by application onto the same tooth surface of a second component containing hydrogen peroxide or a hydrogen peroxide precursor. The sequence of application of such components may also be reversed depending upon the desired application. Such a sequential application would provide for the production of peroxyacetic acid in situ and is advantageously beneficial to accessing chromogens in tooth structures.

According to a n additional aspect of the present invention, the first component containing a source o f acetyl groups is applied to the tooth and is allowed for a sufficient time period to penetrate into pores present in the tooth structure. The second component containing the peroxide precursor is then applied which then advantageously provides for the generation of peroxyacid at locations deep within the tooth structure to thereby interact with chromogens that may also be within the tooth structure resulting in enhanced tooth whitening.

The hydrogen peroxide precursor for use in connection with the present invention is preferably selected from the group consisting of carbamide peroxide, sodium percarbonate, sodium perborate, calcium peroxide, magnesium peroxide, sodium peroxide, and the anhydrous poly(vinyl pyrrolidone)/hydrogen peroxide complexes. It is contemplated that any compound which, when in contact with water, is capable of generating, converting to, or otherwise becoming hydrogen peroxide or peroxide anion, will have utility in the formulation of the present inventive compositions. For instance, it is possible to utilize other alkali metal percarbonates (such as potassium percarbonate), as well as enzymatic sources of hydrogen peroxide, such as glucose oxidase in combination with beta-D-glucose. Additional useful peroxide precursors will become apparent to those skilled in the art based upon the present disclosure.

The peroxide precursor is present in the compositions of the present invention as they are applied directly to the tooth surface in an amount sufficient to result in a hydrogen peroxide concentration of from about 0.1 percent by weight to about 15 percent by weight. Higher levels of hydrogen peroxide may be used in conjunction with a supervised dental whitening procedure in which the soft tissue (i.e., the gingival and other mucosal surfaces) are physically isolated from the teeth being whitened. Hydrogen peroxide concentrations up to about 3 percent are acceptable for short-term (less than 60 minutes) incidental contact with soft tissue.

Compositions that utilize hydrogen peroxide itself, rather than a precursor, should be prepared as two or more components, keeping the source of acetyl groups in one component and hydrogen peroxide in the second component as an aqueous solution containing both hydrogen peroxide and the source of acetyl groups will quickly form a peroxyacid.

The source of labile acetyl groups of the present invention is a $C_1$–$C_5$ molecule having between 1 to 5 labile $C_1$–$C_5$ acyl containing groups. According to a preferred embodiment, the source of labile acetyl groups is a $C_1$–$C_3$ molecule having 1, 2, or 3 acetyl groups. According to a specific preferred embodiment of the present invention, the source of labile acetyl groups is glyceryl triacetate, glyceryl diacetate or glyceryl acetate. The source of labile acetyl groups is present in the compositions of the present invention in an amount sufficiently high to allow for the rapid generation of peroxyacid, i.e. in an amount between about 0.1 percent by weight to about 6.0 percent by weight of the composition.

Glyceryl triacetate (CAS No. 102-76-1) has a molecular weight of about 218.20 and is available as a colorless, oily liquid with a slight fatty odor. It is soluble in water up to a concentration of approximately 7.1% by weight in.water and is generally prepared by the acetylation of glycerol. Glyceryl triacetate has an extremely low order of toxicity and is listed as GRAS (Generally Regarded as Safe as a direct food additive) in the Code of Federal Regulations, Title 21, Part 184.1901. It is therefore ideally suited for use in oral care products.

The use of glyceryl triacetate is advantageous due to its highly labile acetyl functionalities (which is important to obtaining effective tooth whitening levels of peroxyacetic acid in the presence of hydrogen peroxide), its low level of oral toxicity, and its unexpected ability to penetrate into intact tooth enamel upon contact to a tooth surface. Additionally, glyceryl triacetate degrades, in the presence of peroxide, into acetic acid (after first converting to peroxyacetic acid), water, and other degradation products that are toxicologically acceptable.

While not wishing to be bound to any particular theory, the tightly packed crystal structure of tooth enamel and, to a lesser degree, dentin renders the tooth relatively impermeable to high molecular weight compounds such as proteins and polysaccharides. In addition, both the hydroxyapatite crystals and their supporting collagen matrix act as permselective barriers to diffusion of many types of molecules. In particular, highly polar or strongly charged ionic species (such as amines and glycols) do not penetrate the tooth structure to the same degree as relatively non-polar or uncharged species. The source of labile acetyl groups advantageously has a sufficiently low molecular weight which allows it to penetrate pores within teeth. Suitable compounds will have molecule weights below 1000, preferably below 500 and most preferably in a range similar to glyceryl triacetate, i.e. between 300 and 100.

It should be noted that the use of slowly or minimally soluble peroxyacid precursors in connection with the composition of the present invention is also useful in applications where the need for immediate release or generation of the peroxyacid just prior to or during use is not required.

According to an additional embodiment, the pH of the tooth whitening composition may be controlled during use as the generation of peroxyacid from hydrogen peroxide and glyceryl triacetate is pH-dependent.

The composition of the present invention may be applied to the stained tooth surface as liquids, gels, pastes, sprays, or as solid delivery systems (for instance, chewing gum or dental floss). The composition may be applied to the tooth surface in the form of a single component anhydrous formulation, a multi-component anhydrous or aqueous formulation mixed prior to application, or a multi-component anhydrous or aqueous formulation mixed directly on the tooth surface by sequential application of two or more components.

The peroxyacids of the present invention advantageously possess a high degree of antimicrobial activity. Accordingly, the compositions of the present invention are envisioned to have useful antimicrobial activity in addition to the desired tooth whitening effects. This activity may cause the destruction of oral microorganisms responsible for the formation of plaque (and eventually tartar), thus adding significantly to the potential utility of the present invention.

In one embodiment, the single component composition remains relatively anhydrous to prevent premature generation of peroxyacetic acid from the interaction of hydrogen peroxide with glyceryl triacetate in aqueous solution. As the composition is anhydrous, it is necessary to utilize a hydrogen peroxide precursor, such as those provided above, which is not only soluble or dispersible, but stable in the carrier.

Carriers for inventive single component compositions should be toxicologically benign and include glycerin, propylene glycol, and polyethylene glycols. Such carriers may include chewing gum and gum base products, and floss carriers and floss wax products. An oil-based carrier is also useful, especially when combined with a surfactant capable of emulsifying the composition upon contact with water. Such oils include both vegetable and mineral oils, in addition to their higher molecular weight counterpart waxes and esters. Carriers for multi-component compositions include all of the above in addition to water. It is to be understood that additional useful carriers will become apparent to those skilled in the art based upon the disclosure herein. The carrier portion of the inventive compositions, which may be composed of one or more individual components, and which may include such components as thickeners, buffering compounds, chelating agents, stabilizers, surfactants, sweeteners, and flavorants, is present at a level of from about 79 percent of the composition (in the form as it is applied to the tooth surface) to about 99.8 percent of the composition.

A thickener may also be added to increase contact time of either the single or multi-component composition on the tooth surface. This is particularly useful in tooth whitening methods where a dental tray is used to confine the material to a patient's dentition. Thickeners such as neutralized carboxypolymethylene and other polyacrylic acid polymers and copolymers, hydroxypropylcellulose and other cellulose ethers, salts of poly(methyl vinyl ether-co-maleic anhydride), poly(vinylpyrrolidone), poly(vinylpyrrolidone-co-vinyl acetate), silicon dioxide, fumed silica, stearic acid esters, and others are found to have utility in the formulation of tooth whitening compositions. The level of thickener, when present, is highly dependent upon the type chosen, but in general is included in the composition at a concentration of from about 0.5 percent by weight to about 20.0 percent by weight of the composition. It is to be understood that additional useful thickeners will become apparent to those skilled in the art based upon the disclosure herein.

The compositions of the present invention may also contain a buffer to provide a specific pH for optimal penetration of the composition into tooth enamel or to provide for optimal generation of peroxyacetic acid from the hydrogen peroxide precursor and glyceryl triacetate. Suitable buffers include sodium hydroxide, potassium hydroxide, ammonium hydroxide, sodium phosphate di- and tri-basic, potassium phosphate di- and tri-basic, sodium tripolyphosphate, tris(hydroxymethyl)aminomethane, triethanolamine, polyethylenimine, and other alkaline buffers. Within a particular formulation, an alkaline buffer may also serve the purpose of neutralizing carboxylic acid side chains in thickening polymers such as polyacrylic acid and poly(methyl vinyl ether-co-maleic anhydride). Acid buffers, such as citric acid, phosphoric acid, and others may also be used alone or in conjunction with an alkaline buffer to obtain the desirable pH and to provide buffering capacity. The level of buffer, when present, is from about 0.5 percent by weight to about 3.0 percent by weight of the composition. It is to be understood that additional useful buffers will become apparent to those skilled in the art based upon the disclosure herein.

The formation of peroxyacetic acid from hydrogen peroxide and glyceryl triacetate has been determined to occur most readily at pH levels in excess of about 5.2. However, peroxyacetic acid is only stable at an acid pH if formulated fully within a composition. Therefore, it is seen to be preferred to provide compositions that generate peroxyacetic acid in situ at a pH more suited to producing it quickly for use in the oral cavity. In this manner, tooth stains can be removed at a much more rapid rate through the use of the present compositions.

Compositions of the present invention may optionally contain one or more chelating agents for the purpose of scavenging metal ions in the composition arid during use of the composition. Metals, such as iron, manganese, and copper, and their oxides are known in the art to cause the degradation of hydrogen peroxide through Fenton-type reactions. This particular degradation mechanism is undesirable in that the hydroxyl free radical (OH°) is created and is not as effective as the perhydroxyl anion (HOO—) in attacking chromogens. Therefore, it is desirable to encourage the dissociation of hydrogen peroxide into perhydroxyl anions, rather than hydroxyl radicals, in order to maximize the effectiveness of the inventive compositions. It may also be desirable to provide conditions in the inventive compositions which are conducive to the formation of peroxyacetic acid ($CH_3COOOH$) and its dissociated species, the peroxyacetate anion ($CH_3COOO—$). In a similar fashion as above, the peroxyacetate anion is much more effective as a bleaching or whitening agent than free radical species, such as the peroxyacetyl radical ($CH_3COOO°$), which form in the presence of metal ions and their oxides.

Although virtually any chelating agent capable of sequestering metal ions in aqueous solution may be advantageously employed for the purpose above, particularly useful chelating agents are selected from the group of phosphonic acids, EDTA, and polyphosphates. In particular, 1,1-dihydroxyethyliene-1-disphosphonic acid (sold by the Monsanto Corp under the trade name Dequest 2010) is seen to provide the desired metal chelating abilities, thereby protecting against free radical formation through Fenton-type reactions. The phosphonic acids are particularly suitable as chelating agents due to their excellent stability in the presence of peroxides. The level of chelating agent, when present, is from about 0.01 to about 5.0 percent by weight of the composition. It is to be understood that additional useful chelating agents will become apparent to those skilled in the art based upon the disclosure herein.

Surface active agents (surfactants) may be used to lower the surface tension of the compositions. Lowering of the surface tension allows for better wetting and spreading of the composition on the tooth surface. Some surfactants, such as zwitterionic and fluorinated surfactants, have been seen to increase the penetration of the present inventive compositions into the tooth structure. Useful surfactants include those identified in U.S. Pat. No. 5,279,816 and U.S. Pat. No. 5,302,375 each incorporated herein by reference in its entirety. It is to be understood that additional useful surfactants will become apparent to those skilled in the art based upon the disclosure herein. The level of surfactant, when present, is from about 0.1 to about 2.0 percent by weight of the composition.

Flavorants may also be included in the oral composition in order to improve palatability and acceptance by the patient or consumer. Flavorants are generally known in the art and include, among others, spearmint, peppermint, anethole, menthol, citrus flavors, and vanilla. It may be desirable to provide within the composition an artificial sweetener selected from the group of sodium saccharin and potassium acesulfame. Both flavorants and sweeteners, when present, are each included at a level of from about 0.05 to about 1.5 percent by weight of the composition. Other artificial sweeteners are contemplated to have utility in the practice of the present invention, limited only by their solubility and stability in the compositions.

Other ingredients may also be added to the compositions of the present invention such as pyrophosphate salts, peroxide stabilizers, soluble and insoluble calcium compounds disclosed in U.S. Pat. No. 5,279,816 and U.S. Pat. No. 5,302,375. In addition, antimicrobial compounds may also be added to the compositions of the present invention in amounts sufficient to have an antimicrobial effect.

The following examples are set forth as representative of the present invention. These examples are not to be construed as limiting the scope of the invention as these and other equivalent embodiments will be apparent in view of the present disclosure, tables and accompanying claims.

EXAMPLE I

In order to determine the ability of the inventive compositions to eliminate tooth stain, a preliminary in vitro study on stained bovine enamel was performed.

Squares of dental enamel 4 mm on a side were cut, using a diamond-cutting disk, from bovine permanent incisors. Using a mold, the enamel squares were embedded in clear polyester casting resin (NATCOL Crafts Inc., Redlands, Calif.) to provide 1.5 cm square blocks with the labial surface exposed. The top surface of the polyester blocks was ground flush with the leveled labial surface of the enamel squares by means of a dental model trimmer. The surface was then smoothed by hand sanding on 400-grit emery paper using water as the lubricant until all grinding marks were removed. Finally, the top surface of the blocks was hand polished to a mirror finish using a water slurry of GK1072 calcined kaolin (median particle size=1.2 microns) on a cotton cloth. The finished specimens were examined under a dissecting microscope and were discarded if they had surface imperfections.

In preparation for the formation of artificial stained pellicle on the enamel, the specimens were etched for 60 seconds in 0.2M HCl followed by a 30-second immersion in a saturated solution of sodium carbonate. A final etch was performed with 1% phytic acid for 60 seconds, then the specimens were rinsed with deionized water and attached to the staining apparatus.

The pellicle staining apparatus was constructed to provide alternate immersion into the staining broth and air-drying of the specimens. The apparatus consisted of an aluminum platform base which supported a Teflon rod (¾ inch in diameter) connected to an electric motor, which by means of a speed reduction box, rotated the rod at a constant rate of 1.5 rpm. Threaded screw holes were spaced at regular intervals along the length of the rod. The tooth specimens were attached to the rod by first gluing the head of a plastic screw to the back of a specimen. The screw is then tightened within a screw hole in the rod. Beneath the rod was a removable, 300-ml capacity trough, which held the pellicle, staining broth.

The pellicle staining broth was prepared by adding 1.02 grams of instant coffee, 1.02 grams of instant tea, and 0.75 grams of gastric mucin (Nutritional Biochemicals Corp., Cleveland Ohio 44128) to 250 ml of sterilized trypticase soy broth. Approximately 50 ml of a 24-hour *Micrococcus luteus* culture was also added to the stain broth. The apparatus, with the enamel specimens attached and the staining broth in the trough was then placed in an incubator at 37° C. with the specimens rotating continuously through the staining broth and air. The staining broth was replaced once every 24 hours for ten consecutive days. With each broth change the trough and specimens were rinsed and brushed with deionized water to remove any loose deposits. On the eleventh day the staining broth as modified by the addition of 0.03 grams of $FeCl_3 \cdot 6H_2O$, and this was continued with daily broth changes until the stained pellicle film on the specimens was sufficiently dark. Then the specimens were removed from the staining broth brushed thoroughly with deionized water, and refrigerated in a humidor until used.

Absorbance measurements over the entire visible spectrum were obtained using the CIELAB color scale (Commission International de L'Eclairage, Recommendations on uniform color spaces, color difference equations, and psychometric color terms, Supplement 2 to CIE publication 15 (E-13.1) 1971 (TC-1.3), 1978, Paris: Beaurea Central de la CIE, 1978). The CIELAB color scale evaluates color in terms of three axes of a color sphere, called L, a, and b. The "L" value is the axis in the color sphere which relates lightness and darkness on a scale from 0 (black) to 100 (white). The "a" value is the axis which relates color on a yellow to blue scale, with a 0 value in the center of the sphere, positive values toward the yellow, and negative values toward the blue. The "b" value is the axis which relates color on a red to green scale, with a 0 value in the center of the sphere, positive values toward the red, and negative values toward the green.

The stained enamel specimens were allowed to air-dry at room temperature for at least one hour before absorbance measurements were made. Measurements were conducted by aligning the center of a 4-mm square segment of stained enamel directly over the 3-mm aperture of the Minolta spectrophotometer. An average of 3 absorbance readings using the L*a*b* factors were taken for each specimen.

The difference between the pretreatment (baseline) and post-treatment readings for each color factor (L*, a*, and b*) represented the ability of a test solution to eliminate chromogens from the stained teeth.

The overall change in color of stained pellicle was calculated using the CIELAB equation $$\Delta E = [(\Delta L^*)^2 + (\Delta a^*)^2 + (\Delta b^*)^2]^{1/2}$$

The individual components of the L*a*b* scale were also analyzed separately to determine the specific changes in lightness, redness, and yellowness, respectively.

Two solutions, A and B, were prepared from a stock solution of 10% hydrogen peroxide adjusted to a pH of 5.20 with 10% NaOH. Solution A was the same as the stock solution of 10% hydrogen peroxide, while Solution B contained 6% w/w of glyceryl triacetate (FCC grade, Spectrum Chemical, Gardena, Cailf.). Initial color readings were recorded for each bovine enamel sample and the samples were marked either "A" or "B". The samples were immersed in their corresponding solutions and allowed to whiten for periods of 30 minutes. After each 30-minute period, the samples were removed and placed in distilled water for 60 seconds. The samples were then removed, dried, and color readings were taken. Four treatments were performed on one day, followed by a distilled water storage overnight, after which another four treatments were performed, utilizing fresh solutions. Following the eight treatments, the samples were placed in yet another fresh solution and allowed to remain immersed for another 24 hours to achieve their maximum attainable whiteness. The results of the eight 30 minute treatments, along with the data for both the distilled water overnight storage period and the 24 hour immersion, are shown in Table 1 below.

TABLE 1

| Total Treatment Time (minutes) | Sample A | | | Sample B | | | Sample A | Sample B |
| --- | --- | --- | --- | --- | --- | --- | --- | --- |
| | $L_A$ | $a_A$ | $b_A$ | $L_B$ | $a_B$ | $b_B$ | $\Delta E_A$ | $\Delta E_B$ |
| 0 | 48.57 | 3.57 | 13.31 | 46.01 | 4.26 | 14.80 | — | — |
| 30 | 54.79 | 2.38 | 14.21 | 58.17 | 2.14 | 15.88 | 6.40 | 12.39 |
| 60 | 58.22 | 2.00 | 14.94 | 61.05 | 1.69 | 15.98 | 9.91 | 15.30 |
| 90 | 60.39 | 1.63 | 14.79 | 65.53 | 0.55 | 13.38 | 12.09 | 19.92 |
| 120 | 63.57 | 1.08 | 13.76 | 68.51 | 0.11 | 10.68 | 15.21 | 23.25 |
| Distilled water 12 hr | 64.30 | 1.13 | 12.10 | 70.79 | 0.31 | 5.84 | 15.96 | 26.64 |
| 150 | 68.85 | 0.46 | 8.64 | 72.66 | 0.34 | 3.40 | 21.04 | 29.25 |
| 180 | 71.05 | 0.12 | 6.24 | 72.83 | 0.46 | 2.49 | 23.82 | 29.75 |
| 210 | 71.70 | 0.17 | 4.49 | 73.80 | 0.36 | 1.87 | 24.99 | 30.90 |
| 240 | 71.40 | 0.93 | 4.01 | 73.11 | 0.58 | 1.70 | 24.79 | 30.32 |
| 24 hours | 78.06 | 0.17 | 0.54 | 77.53 | 0.29 | 0.60 | 32.32 | 35.30 |

It is clear from the comparative ΔE values above that the stained enamel specimen labeled as sample "B" experienced a much more rapid whitening effect than sample "A", especially following the first few 30-minute treatments. It should be noted that sample B, after four treatments in Solution B containing 10% hydrogen peroxide and 6% glyceryl triacetate, experienced a large decrease in its b value (down to 5.84 from 10.68) during the 12 hour distilled water immersion between treatment days. Such an effect was not observed for sample A which was immersed in the 10% hydrogen peroxide solution alone.

Both specimens seemed to reach a higher degree of whiteness after immersion in their respective solutions for 24 hours, although Specimen B did achieve a ΔE about 10 percent higher than Specimen A.

A number of peroxyacid precursors were compared for their ability to whiten extracted teeth by the method described above. The following solutions were prepared by combining all of the ingredients in separate 4-oz borosilicate glass bottles with screw-on sealing caps.

| Ingredient | Percent (w/w) | | | | |
| --- | --- | --- | --- | --- | --- |
| | A | B | C | D | E |
| Deionized water | 50.0 | 49.5 | 49.5 | 49.5 | 49.5 |
| Anhydrous ethanol | 50.0 | 49.5 | 49.5 | 49.5 | 49.5 |
| Glyceryl triacetate | | 1.0 | | | |
| Acetylsalicylic acid | | | 1.0 | | |
| Tetraacetylethylenediamine | | | | 1.0 | |
| Polly(vinyl pyrollidone-co-vinyl acetate) | | | | | 1.0 |
| TOTAL | 100.0 | 100.0 | 100.0 | 100.0 | 100.0 |

Each of the above solutions was brushed onto the crown surface of an extracted human molar that had been previously graded for tooth shade. All of the teeth had an initial VITA shade of A3 and after treating each tooth with solution, its roots were wrapped with a moist paper towel in order to prevent any color change in the tooth due to dessication. Each tooth crown was then coated with the following gel composition.

| Ingredient | Percent (w/w) |
| --- | --- |
| Distilled water | 73.92 |
| 1-Hydroxyethylidene-1,1-diphosphonic acid | 0.40 |
| Sodium stannate | 0.02 |
| Carbopol 974P | 5.00 |
| Hydrogen Peroxide 35% | 17.14 |
| Ammonium hydroxide (29%) | 3.50 |
| TOTAL | 100.00 |

After 60 minutes, each tooth was graded for color and the following results were recorded.

| Pre-Treat Solution | Initial Shade | Final Shade | Shade Change |
|---|---|---|---|
| A | A3 | A2 | 4 |
| B | A3 | B1 | 8 |
| C | A3 | A2 | 4 |
| D | A3 | A1 | 7 |
| E | A3 | A2 | 4 |

As is evident from the data above, the composition containing the peroxyacid precursor having three labile acetyl functionalities and a low molecular weight, i.e. Sample B containing glyceryl triacetate, generated the most whitening capability. In contrast, the sample containing the high molecular weight species tetraacetylethylenediamine delivered significantly less whitening capability, while the samples containing the high molecular weight species acetylsalicylic acid and poly(vinyl pyrollidone-co-vinyl acetate) delivered dramatically less whitening capability.

Example II

Another test was done to determine the effect of pH on the oral composition of the present invention at a given concentration of hydrogen peroxide. Two solutions, C and D, were prepared from a stock solution of 10% hydrogen peroxide. Solution C was adjusted to a pH of 5.20 with 10% NaOH while solution D was adjusted to a pH of 7.80 with 10% NaOH. Just prior to immersion of the stained bovine enamel specimens into solution, 6% w/w of glyceryl triacetate (FCC grade, Spectrum Chemical, Gardena, Calif.) was added to each solution. Initial color readings were recorded as above and the samples were marked either "C" or "D". The samples were immersed in their corresponding solutions and allowed to whiten for periods of 30 minutes. After each 30-minute period, the samples were removed and placed in distilled water for 60 seconds. The samples were then removed, dried, and color readings were taken as above. Three treatments were performed in sequence. Following the three treatments, the samples were placed in yet another fresh solution and allowed to remain immersed for another 24 hours to achieve their maximum attainable whiteness. The results of the eight 30 minute treatments, along with the data for both the distilled water overnight storage period and the 24 hour immersion, are shown in Table 2 below.

TABLE 2

| Total Treatment Time (minutes) | Sample C | | | Sample D | | | Sample C $\Delta E_C$ | Sample D $\Delta E_D$ |
|---|---|---|---|---|---|---|---|---|
| | $L_C$ | $a_C$ | $b_C$ | $L_D$ | $a_D$ | $b_D$ | | |
| 0 | 56.48 | 4.71 | 18.84 | 58.50 | 4.34 | 17.15 | — | — |
| 30 | 63.83 | 3.48 | 21.11 | 79.09 | 0.78 | 17.32 | 7.78 | 20.90 |
| 60 | 71.45 | 2.11 | 21.11 | 83.50 | −0.42 | 11.24 | 15.30 | 26.13 |
| | | | | | | | | 90 |
| 75.43 | 1.24 | 19.86 | 85.61 | −0.31 | 7.11 | 19.29 | 29.28 | |

It can be seen that sample D, which was soaked in solution D at pH 7.8, performed substantially better than sample C, which was soaked in solution C at pH 5.2.

Example III

A commercially available product used in an office setting by dentists utilizes 35% hydrogen peroxide and corresponds to a composition described in U.S. Pat. No. 5,032,178. A mixture to be applied to a stained tooth surface was prepared according to the manufacturer's instructions and used to determine its ability to remove tooth stain as above (a total of only two applications was done). The results are shown in Table 3 below.

TABLE 3

| Total Treatment Time (minutes) | U.S. Pat. No. 5,032,178 | | | Sample D | | | '178 $\Delta E_{CP}$ | Sample D $\Delta E_D$ |
|---|---|---|---|---|---|---|---|---|
| | $L_{CP}$ | $a_{CP}$ | $b_{CP}$ | $L_D$ | $a_D$ | $b_D$ | | |
| 0 | 60.00 | 3.30 | 15.45 | 58.50 | 4.34 | 17.15 | — | — |
| 30 | 72.58 | 0.69 | 16.74 | 79.09 | 0.78 | 17.32 | 7.78 | 20.90 |
| 60 | 77.11 | −0.05 | 14.86 | 83.50 | −0.42 | 11.24 | 15.30 | 26.13 |

From Table 3, it can be seen that even though the commercial product utilizes 30–35% hydrogen peroxide as an oxidizer, it did not perform as well as solution "D", which contains only 10% hydrogen peroxide and glyceryl triacetate, after two treatments.

Example IV

The following single-component composition was prepared and is representative of a single-component embodiment of the invention.

TABLE 4

| Ingredient | Percent (w/w) |
|---|---|
| Polyethylene glycol 400 | 67.40 |
| Sodium saccharin | 0.50 |
| Glyceryl triacetate | 1.50 |
| Polyvinylpyrrolidone | 10.00 |
| Fumed silica | 12.00 |
| Sodium percarbonate powder | 8.00 |
| Flavor | 0.60 |
| TOTAL | 100.00 |

The above composition was manufactured under a vacuum of 26–26" Hg in a Ross double planetary mixer (Charles Ross & Son, Hauppauge, N.Y.). All product contact parts in the mixer were either KYNAR-coated metal or plastic in order to prevent leaching of contaminant metals (such as iron, copper, and manganese) into the composition during manufacture. KYNAR (a DuPont trademark) is a fluoropolymer coating used to, among other purposes, prevent corrosion of steel or metal parts in the presence of aggressive chemicals. These same product contact parts were also passivated by contacting them with a solution of 10 w/w percent hydrogen peroxide and subsequently rinsed with distilled water just prior to use.

The above composition was prepared by placing the polyethylene glycol into the mixing chamber, adding the sodium saccharin and glyceryl triacetate, and allowing to mix under vacuum at high speed until a clear solution was obtained. The polyvinylpyrrolidone was then added and mixed under vacuum at high speed until homogeneously dispersed. The filmed silica was then added, with slow mixing, to the above phase in the mixing chamber. The addition of the fumed silica resulted in a high degree of thickening of the total mixture. Finally, after the complete homogenization of the above dispersion (the thickened carrier matrix), the sodium percarbonate powder was added and dispersed thoroughly, again under vacuum and high speed mixing. Finally, the flavor was added and completely blended into the mixture, The resulting bleaching composition was a slightly off-white gel. The composition was transferred to polypropylene syringes for storage and testing.

When water was mixed with the inventive composition (in a ratio of approximately 1 part water to 5 parts gel, by weight), the mixture quickly gave off an odor similar to acetic acid (vinegar-type smell), which was indicative of peroxyacetic acid generation. The composition was also placed on the surface of several extracted human teeth, whereby a visible whitening effect was seen after a 60 minute contact time.

Example V

Another embodiment of the present invention, namely dual-component compositions, were prepared in a similar fashion to the manufacturing procedure outlined in Example IV, the only exception being that each component of the dual-component compositions in Table 5 below was prepared, packaged and stored separately, to be combined just prior to application to the tooth surface.

through baffles in the static mixer which force the two components to blend together, and finally emerge from the opposite end of the static mixer as a single, homogeneous mixture. The resulting mixture thus contains both the hydrogen peroxide precursor and glyceryl triacetate, and alternatively, water in a sufficient amount to allow the production of peroxyacetic acid for whitening the teeth.

In order to demonstrate the superior tooth whitening capabilities of the inventive compositions, tests on extracted human teeth were performed, whereby measurements of changes in qualitative color (VITA Shade Guide measurements, a method well known in the art) were taken.

When mixed at a 1 to 1 weight ratio as described above (forced under pressure through a static mixer syringe tip), all of the above compositions generated peroxyacetic acid. A small amount of each mixed composition was placed on the surface of an extracted human molar which had been graded as to VITA shade color prior to treatment. After a period of approximately 60 minutes, a visible color change was observed on each of the molars.

TABLE 5

| | Percent (w/w) | | | | | |
|---|---|---|---|---|---|---|
| | A | | B | | C | |
| Ingredient | 1 | 2 | 1 | 2 | 1 | 2 |
| Propylene glycol | 42.56 | 45.00 | | | | |
| Polyethylene glycol 400 | | | | | 70.00 | 73.40 |
| Polyethylene glycol 600 | 23.00 | 33.90 | | | | |
| Glycerin | 5.00 | 5.00 | 5.00 | 5.00 | | |
| Distilled water | 2.67 | | 69.24 | 82.80 | | |
| Sodium saccharin | | 0.80 | | | | 0.80 |
| Potassium acesulfame | | | | 1.00 | | |
| Dequest 2010 | 0.10 | | 0.40 | | | |
| Sodium stannate | | | 0.02 | | | |
| Flavor | | 0.80 | | 1.00 | | 1.20 |
| Carbopol 974P | 2.00 | 2.00 | 5.00 | 5.00 | | |
| Hydroxypropylcellulose | 10.00 | 10.00 | | | | |
| Polyvinylpyrollidone | | | | | 10.00 | 10.00 |
| Fumed silica | | | | | 12.00 | 12.00 |
| Poly(vinylpyrollidone-co vinyl acetate) | | | | | | 1.00 |
| Sodium hydroxide monohydrate | 2.67 | | | | | |
| Ammonium hydroxide 29% | | | 3.20 | 3.20 | | |
| Carbamide peroxide | 12.00 | | | | | |
| Sodium percarbonate powder | | | | | 8.00 | |
| Hydrogen peroxide 35% | | | 17.14 | | | |
| Glyceryl triacetate | | 2.50 | | 2.00 | | 1.60 |
| TOTAL | 100.00 | 100.00 | 100.00 | 100.00 | 100.00 | 100.00 |

After manufacture, each of the above compositions was placed in a separate chamber of a dual-chamber syringe, the type having a plunger mechanism whereby externally applied pressure to the plunger forces each of the two components through a mixing chamber (known in the art as a static mixer) attached to the end of the dual-chambered syringe. A further description of this method of combining and mixing two incompatible components for the purpose of bleaching teeth can be found in the copending U.S. patent application Ser. No. 09/054,156 filed Apr. 2, 1998 hereby incorporated by reference in its entirety. Just prior to use, the two separate components are forced by the externally applied pressure into one end of the static mixer, travel Example VI A further embodiment of the present invention provides for the combination of a hydrogen peroxide precursor and glyceryl triacetate in situ. In this mode of applying the inventive compositions, a first composition containing one of either the hydrogen peroxide element or the glyceryl triacetate element is placed directly onto the tooth surface to be whitened. A period of time may be allowed for the first element to penetrate into the tooth structure. Then, a second composition containing the remaining inventive composition element is placed directly onto the same tooth surface that has already been contacted with the first composition. In this manner, both the hydrogen peroxide precursor element and the glyceryl triacetate element are present on the stained tooth surface simultaneously. Peroxyacetic acid is thereby generated on and within the stained tooth providing a method of applying the inventive compositions (and whitening teeth in general) having certain advantages over other approaches.

Since peroxyacids (and peroxides in general) are highly reactive species, an in situ method of applying and subsequently generating oxidizing agents on and within a stained tooth surface is advantageous. By generating the peroxyacid (in this invention, peroxyacetic acid) on and within the tooth (thus in intimate contact with the stain-causing molecules themselves), superior tooth whitening results may be obtained. Although not wishing to be bound by any particular theory, it is believed that deeper penetration into the tooth structure by a first element (one of either a hydrogen peroxide precursor composition or a glyceryl triacetate composition) prior to contact with the second element will generate peroxyacetic acid (upon placement of the second remaining element) at the same site reached by the first element. In this manner, the depth at which tooth whitening occurs by the inventive compositions may be controlled. The in situ method described above has an additional advantage, in that the amount of peroxyacetic acid can be limited to that amount formed within the tooth structure itself (i.e. only where both of the required elements are present simultaneously). Accordingly, one aspect of the present invention involves the application of a composition or component of the composition onto the tooth surface and then allowing the composition or a first component of the composition to penetrate within the tooth structure itself. Peroxyacid is then allowed to generate within the tooth structure by application of an aqueous solution or a second component capable of reacting with the first component to generate a peroxyacid.

This in situ tooth whitening method may also be used with other peroxyacid precursors other than, and/or in addition to, glyceryl triacetate. Such peroxyacid precursors include all water-soluble or partially water-soluble compounds containing at least one acetyl group functionality, including, but not limited to acetylated amino acids (such as acetyl cysteine, acetyl glycine, etc) and acetylated polymers. Due to the desired penetration into the tooth structure in order to reach deeper stains, low molecular weight (<1000) acetyl group-containing molecules are preferred.

Example VII

A single-component toothpaste containing a very low level of water was prepared that contained glyceryl triacetate, together with sodium percarbonate as a hydrogen peroxide precursor.

| Ingredient | Percent (w/w) |
| --- | --- |
| Polyethylene glycol 400 | 34.76 |
| Polyethylene glycol 3350 | 1.00 |
| Water | 1.80 |
| Glyceryl triacetate | 2.00 |
| Sodium percarbonate | 5.00 |
| Sodium bicarbonate | 50.00 |
| Hydrated silica | 1.60 |
| Sodium lauryl sulfate | 0.60 |
| Sodium methyl cocoyl taurate | 0.60 |
| Sodium fluoride | 0.24 |
| Sodium saccharin | 1.20 |
| Flavor | 1.20 |
| TOTAL | 100.00 |

The above composition was manufactured in a manner similar to that described in the Examples above and packaged in plastic tubes. Upon extruding a small amount of the toothpaste and combining it with water at a ratio of 1 part by weight toothpaste to 1 part by weight water, an immediate odor of peroxyacetic acid was evident.

Example VIII

Chewing gum containing a thin slurry coating of sodium percarbonate and glyceryl triacetate in vegetable oil was prepared. A slurry of sodium percarbonate was first made by manually stirring approximately 2.0 percent by weight of sodium percarbonate powder (Solvay FB100) into a mixture of 20 parts highly refined avocado oil (Super Refined Avocado Oil, Croda, Inc) and 1 part glyceryl triacetate (by volume). A portion of the resulting slurry (approximately 0.30 grams) was brushed onto the surface of a stick of a commercially available chewing gum (Extra, Wm. Wrigley & Son, Chicago, Ill.) and allowed to absorb overnight.

When manually kneaded in the presence of surface moisture provided by dabbing the gum bolus onto a wet surface, a slight odor of peroxyacetic acid was detected after about 30 seconds. It is expected that a similar result would be obtained upon chewing a stick of gum similarly prepared, thus providing peroxyacetic acid to the oral cavity, including the surface of the teeth.

It is anticipated that other modes of applying, blending, combining, and otherwise mixing together the components of chewing gum with the inventive components, namely a hydrogen peroxide precursor and glyceryl triacetate will result in a solid, chewable object capable of generating peroxyacetic acid upon contact with moisture from saliva.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention.

What is claimed is:

1. A composition comprising:
an orally acceptable, tooth whitening peroxyacetic acid generating mixture including a source of hydrogen peroxide and an acetic acid ester of glycerin, wherein the source of hydrogen peroxide and the acetic acid ester of glycerin are dispersed within an orally acceptable anhydrous carrier further comprising a flavorant or sweetener, wherein said flavorant improves the palatability and oral acceptability of said composition.

2. The composition of claim 1 wherein the acetic acid ester of glycerin is selected from the group consisting of glyceryl triacetate, glyceryl diacetate and glyceryl acetate.

3. A composition according to claim 1 wherein the source of hydrogen peroxide is selected from the group consisting of carbamide peroxide, sodium percarbonate, sodium perborate, calcium peroxide, magnesium peroxide, sodium peroxide, and anhydrous poly(vinyl pyrrolidone)/hydrogen peroxide complexes.

4. A composition according to claim 1 capable of providing an oral pH of more than 5.2 to generate peroxyacetic acid.

5. A composition according to claim 4, wherein the oral pH is 7.8.

6. The composition of claim 1 wherein the orally acceptable anhydrous carrier is selected from the group consisting of glycerin, propylene glycol, polyethylene glycols, chewing gum and gum base products, floss carriers and floss wax products, mineral oils, vegetable oils, waxes and esters.

7. The composition of claim 1 wherein the orally acceptable anhydrous carrier comprises a thickening agent.

8. The composition of claim 4 wherein the thickening agent is selected from the group consisting of neutralized carboxypolymethylene, polyacrylic acid polymers and copolymers, hydroxypropylcellulose and other cellulose ethers, salts of poly(methyl vinyl ether-co-maleic anhydride), poly(vinylpyrrolidone), poly(vinylpyrrolidone-co-vinyl acetate), silicon dioxide, fumed silica, and stearic acid esters.

9. The composition of claim 1 wherein the orally acceptable anhydrous carrier comprises a buffer.

10. The composition of claim 9 wherein the buffer is selected from the group consisting of sodium hydroxide, potassium hydroxide, ammonium hydroxide, sodium phosphate di- and tn-basic, potassium phosphate di- and tri-basic, sodium tripolyphosphate, tris (hydroxymethyl) aminomethane, triethanolamine, polyethylenimine, polyacrylic acid, poly (methyl vinyl ether-co-maleic anhydride), citric acid, and phosphoric acid.

11. The composition of claim 1 wherein the orally acceptable anhydrous carrier comprises a surfactant.

12. The composition of claim 11 wherein the surfactant is selected from the group consisting of zwitterionic and fluorinated surfactants.

13. The composition of claim 1 wherein the orally acceptable anhydrous carrier comprises a chelating agent.

14. The composition of claim 13 wherein the chelating agent is selected from the group consisting of phosphonic acids, EDTA, and polyphosphates.

15. A method for whitening teeth comprising:
applying one of either a glyceryl triacetate or a source of hydrogen peroxide onto a tooth surface; and
applying the other of the remaining glyceryl triacetate or source of hydrogen peroxide onto the same tooth surface, so as to generate peroxyacetic acid upon contact with an aqueous solution on the surface of the tooth.

16. A method for cosmetically treating teeth comprising the steps of:
applying a C1–C5 molecule having between 1 to 5 labile C1–C5 acetyl containing groups onto the surface of a tooth;
allowing the C1–C5 molecule having between 1 to 5 labile C1–C5 acetyl containing groups to penetrate into the tooth;
applying a source of peroxide onto the surface of the tooth; allowing the C1–C5 molecule having between 1 to 5 labile C1–C5 acetyl containing groups to react with the source of hydrogen peroxide to generate a peroxyacid within the tooth; and
allowing the peroxyacid to effect whitening of the tooth.

17. The method of claim 16 wherein the C1–C5 molecule having between 1 to 5 labile C1–C5 acetyl containing groups has a molecular weight of between about 100 to about 300.

18. The method of claim 16 wherein the C1–C5 molecule having between 1 to 5 labile C1–C5 acetyl containing groups has a molecular weight approximate that of glyceryl triacetate.

19. A composition for whitening teeth in an oral cavity comprising:
a source of hydrogen peroxide in an amount that results in about 0.1% to about 15.0% of hydrogen peroxide when applied to the oral cavity;
an acetic acid ester of glycerin in an amount of about 0.1% to about 6.0%; and
an orally acceptable anhydrous carrier in an amount of about 79.0% to about 99.8%;
wherein the percentages are weight to weight of the composition.

20. The composition of claim 19 wherein the acetic acid ester of glycerin is selected from the group consisting of glyceryl triacetate, glyceryl diacetate and glyceryl acetate.

21. A composition according to claim 19, wherein the source of hydrogen peroxide is selected from the group consisting of carbamide peroxide, sodium percarbonate, sodium perborate, calcium peroxide, magnesium peroxide, sodium peroxide, and anhydrous poly(vinyl pyrrolidone)/hydrogen peroxide complexes.

22. The composition of claim 19, wherein the orally acceptable anhydrous carrier is selected from the group consisting of glycerin, propylene glycol, polyethylene glycols, chewing gum and gum base products, floss carriers and floss wax products, mineral oils, vegetable oils, waxes and esters.

23. The composition of claim 19, wherein the orally acceptable anhydrous carrier comprises a thickening agent in an amount of about 0.5% to about 20.0%.

24. The composition of claim 23, wherein the thickening agent is selected from the group consisting of neutralized carboxypolymethylene, polyacrylic acid polymers and copolymers, hydroxypropylcellulose and other cellulose ethers, salts of poly(methyl vinyl ether-co-maleic anhydride), poly(vinylpyrrolidone), poly(vinylpyrrolidone-co-vinyl acetate), silicon dioxide, fumed silica, and stearic acid esters.

25. The composition of claim 19, wherein the orally acceptable anhydrous carrier comprises a buffer in an amount of about 0.5% to about 3.0%.

26. The composition of claim 25, wherein the buffer is selected from the group consisting of sodium hydroxide, potassium hydroxide, ammonium hydroxide, sodium phosphate di- and tn-basic, potassium phosphate di- and tri-basic, sodium tripolyphosphate, tris(hydroxymethyl)aminomethane, triethanolamine, polyethylenimine, polyacrylic acid, poly(methyl vinyl ether-co-maleic anhydride), citric acid, and phosphoric acid.

27. The composition of claim 19, wherein the orally acceptable anhydrous carrier comprises a surfactant in an amount of about 0.1% to about 2.0%.

28. The composition of claim 27, wherein the surfactant is selected from the group consisting of zwitterionic and fluorinated surfactants.

29. The composition of claim 19, wherein the orally acceptable anhydrous carrier comprises a chelating agent in an amount of about 0.01% to about 5.0%.

30. The composition of claim 29, wherein the chelating agent is selected from the group consisting of phosphonic acids, EDTA, and polyphosphates.

31. The composition of claim 19, wherein the orally acceptable anhydrous carrier comprises flavorants or sweeteners in an amount of about 0.05% to about 1.5%.

32. The composition of claim 20, wherein the acetic acid ester of glycerin comprises glyceryl triacetate in an amount of about 6.0%.

* * * * *